United States Patent [19]

Fraenkel et al.

[11] Patent Number: 4,921,777
[45] Date of Patent: * May 1, 1990

[54] METHOD FOR MANUFACTURE OF MULTILAYER PRINTED CIRCUIT BOARDS

[75] Inventors: Howard A. Fraenkel, Lebanon; Joseph M. Ilardi, Sparta; Bruce E. Kurtz, Lebanon, all of N.J.; Frank A. Spicciati, Liverpool, N.Y.

[73] Assignee: Allied-Signal Inc., Morris Township, N.J.

[*] Notice: The portion of the term of this patent subsequent to Jan. 30, 2007 has been disclaimed.

[21] Appl. No.: 225,671

[22] Filed: Aug. 1, 1988

Related U.S. Application Data

[63] Continuation-in-part of Ser. No. 80,932, Aug. 3, 1987, abandoned.

[51] Int. Cl.⁵ .............................................. G03C 5/16
[52] U.S. Cl. ..................................... 430/314; 430/316; 430/317; 430/319; 430/394; 204/15
[58] Field of Search ............... 430/312, 313, 314, 315, 430/316, 317, 318, 319, 394

[56] References Cited

U.S. PATENT DOCUMENTS

| | | | |
|---|---|---|---|
| 4,211,603 | 7/1980 | Reed | 156/659.1 |
| 4,528,259 | 7/1985 | Sullivan | 430/312 |
| 4,582,778 | 4/1986 | Sullivan | 430/273 |
| 4,795,693 | 1/1989 | Ors et al. | 430/312 |

Primary Examiner—Jose Dees
Attorney, Agent, or Firm—Ernest D. Buff; Gerhard H. Fuchs; Richard C. Stewart

[57] ABSTRACT

This method relates to a process for manufacturing printed circuit boards in which a metal coating is sputtered onto certain regions of a substrate. Adhesion of the sputtered material is excellent. Surface preparation of the substrate and etching thereof prior to sputtering are virtually eliminated. Films deposited by sputtering exhibit uniform coverage and thickness.

21 Claims, 3 Drawing Sheets

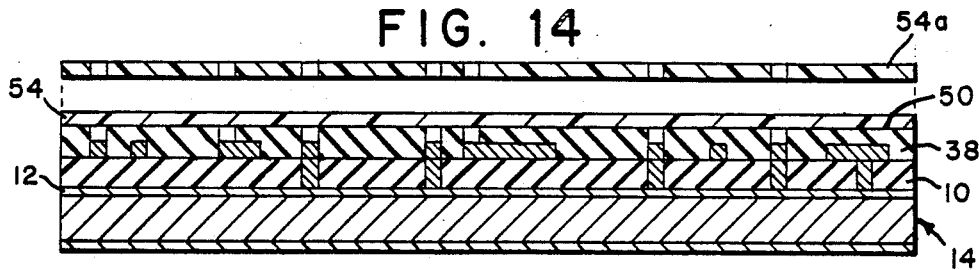
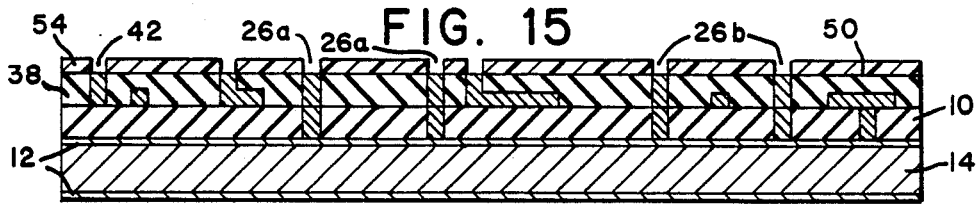
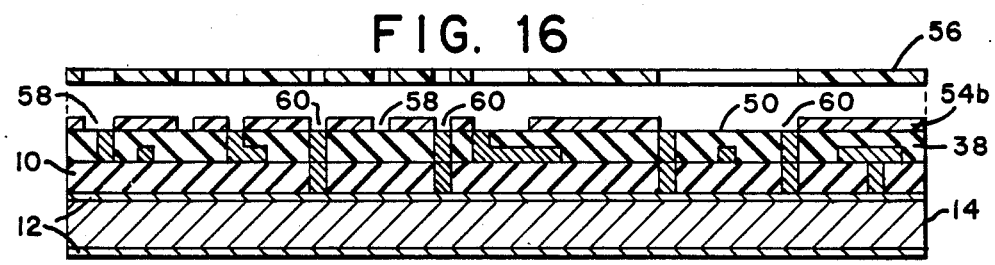
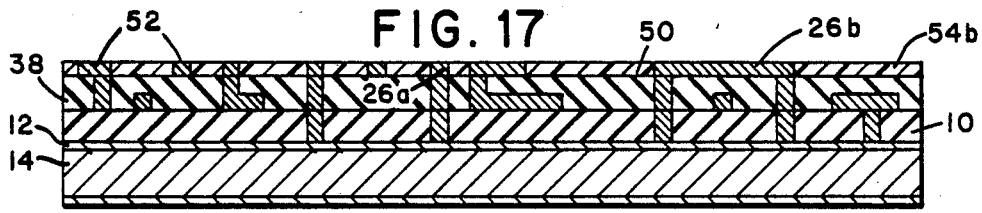
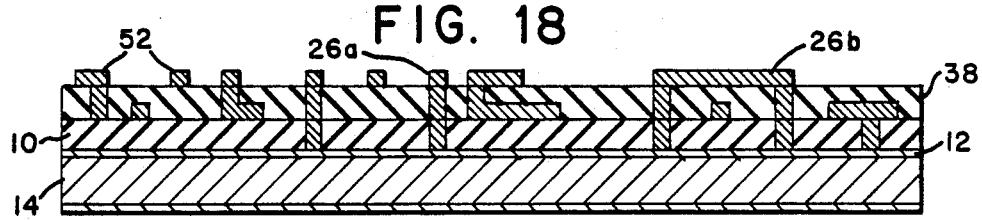
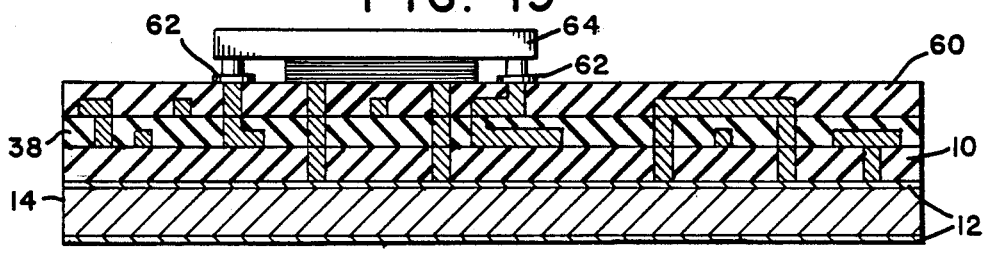

METHOD FOR MANUFACTURE OF MULTILAYER PRINTED CIRCUIT BOARDS

CROSS REFERENCE TO RELATED APPLICATIONS

This is a continuation-in-part of U.S. application Ser. No. 080,932, filed Aug. 3, 1987.

BACKGROUND OF THE INVENTION

1. Field of the Invention

This invention relates to a process for manufacturing multilayer printed circuit boards. Another aspect of this invention relates to printed circuit boards manufactured by the process of this invention.

2. Prior Art

Many methods are known for the preparation of multilayer printed circuits. In many older techniques conductive holes are introduced through printed circuit boards to accommodate insertion and soldering of electrical component leads and for making electrical connections between two or more circuit patterns. Holes are conventionally drilled or punched through a copper clad, rigid board followed by a plating procedure, e.g., a copper reduction procedure such as that disclosed in "Printed Circuits Handbook" edited by Clyde F. Coombs, Jr., published by McGraw-Hill Book Company, New York, NY, 1967, Chapter 5. The copper clad board with plated through-holes can then be processed into printed circuit boards using resists and processes disclosed in "Printed Circuits Handbook", supra or in U.S. Pat. No. 3,469,982. A disadvantage of the conventional copper reduction procedure for plating holes is a waste of expensive catalyst which adheres not only to the hole walls but to the copper cladding, resulting in superfluous overplating of the copper cladding.

The preparation of multilayered printed circuit boards using a photohardenable film and additive printing process is described in U.S. Pat. Nos. 4,054,479 and 4,054,483. The conductive interconnections between the layers are produced by predrilling holes in a photosensitive element and registering the holes with underlying printed circuit patterns Such predrilling procedures by their inherent inaccuracies of registration are limited to printed circuit patterns where circuit lines are not closely spaced.

U.S. Pat. No 4,157,407 describes a process for preparing printed circuits with electrical interconnections without drilling or punching the requisite hole and without using the time consuming hole chemical catalyzation process of the prior art. Multilayered circuits can be provided by this process which have high packing density with multiple crossovers and interconnections or vias. The process of U.S. Pat. No. 4,157,407, while effective for the preparation of multilayered circuits, requires many repetitive steps in practical use including: two registrations of the image and exposure to actinic radiation: two applications of finely divided metal, including application to the through-holes: two applications of heat: and two removals of excess metal particles, e.g., by water-wash followed by drying.

U S. Pat. No 4,469,777 describes a process for preparing a two layer printed circuit having conductive interconnections wherein at least one layer of a photoadhesive composition is applied to a substrate bearing an electrically conductive circuit pattern and exposing said photoadhesive layer or layers through a circuit image of three different optical densities, i.e., zero, gray and opaque, removing portions of the photosensitive layer by solvent washout, applying finely divided metal, alloy or plating catalyst to adherent image areas, optionally curing the printed circuit, e.g., heating or ultraviolet exposure and plating to form an interconnected electrically conductive circuit pattern. U.S. Pat. No. 4,469,777 states that multilayer printed circuits can also be prepared by repeating the steps using additional layers of photoadhesive material.

U.S. Pat. No. 3,934,335 describes a process in which multilayer printed circuit boards are fabricated by coating a suitable substrate, metal, plastic paper, with a photosensitive coating, exposing the photosensitive coating to form a dielectric thereof, coating the dielectric layer with a coating of a photosensitive chemical solution, selectively imaging and developing the photosensitive coating to form a desired circuit pattern on the dielectric coating, forming a first layer of circuitry by coating the circuit pattern with a conducting material, coating the circuitry bearing layer with a second layer of photosensitive material, selectively exposing and developing the second layer of photosensitive material to form a dielectric with open windows to the first circuit layer, coating the second dielectric layer of the first circuitry with a coating of photosensitive chemical solution, selectively imaging and developing the coating of photosensitive chemical solution to form a circuit pattern and an interconnect pattern and forming a conductor layer of circuitry and interconnects, the interconnect metallization connecting the second circuitry layer with the first circuitry layer, repeating the process to form additional circuitry layers to perform a desired electrical function and forming on the last dielectric layer a metallization such as either a solder mask for circuit terminals or a ground plane and thereafter either retaining the substrate if desired as for example, a heat sink or additional support or both, or removing the substrate to form a very light weight multilayer printed circuit board.

U.S. Pat. No. 4,159,222 describes the method of manufacturing printed circuitry with sufficiently high resolution to permit line densities of at least 1 mil lines on 3 mil centers includes the steps of placing a thickness of dry film photoresist on a smooth, polished substrate or carrier optionally, applying a thin lubricating layer of spray wax to the exposed surface of the photoresist, wringing a mask defining a desired conductive circuit pattern into high integrity, intimate contact with the surface of the resist, exposing and developing the resist to remove the resist from the smooth surface in regions where the conductive circuit pattern is to be formed, electroplating the conductors within the voids formed in the resist: removing all remaining resist, laminating a flowable dielectric material to the smooth surface of the substrate and the conductive circuit pattern, and removing the laminate material and conductive circuit pattern from the smooth surface.

U.S Pat. No 4,159,222 also states that if desired, conductive via interconnects can be selectively formed and additional layers of circuit patterns can be formed atop the first high resolution layer.

U.S. Pat. No. 4,306,925 describes a process for the manufacture of high density printed circuits by forming a first conductive circuit pattern on a polished temporary substrate, forming a second conductive circuit pattern (which may be an interconnect pattern) on the first pattern if desired, laminating a flowable insulator material to the first and second conductive circuit layers and temporary substrate to form first and second insulator layers, sanding to form a smooth top surface coplanar with the top of the top conductive pattern, selectively adding additional layers and a substrate and stripping the printed circuit from the temporary substrate. The conductive patterns may be formed with high resolution using photolithographic techniques.

SUMMARY OF THE INVENTION

One aspect of this invention relates to a process for manufacturing a printed circuit board. More particularly, the process of this invention comprises the steps of:

(a) applying a first layer of a radiation curable dielectric material to a given area of a substrate;

(b) placing a photomask defining a first conductor circuit pattern adjacent to the surface of said first layer of said radiation curable dielectric material;

(c) exposing said material to a source of radiation and developing said material to expose those regions of said substrate where a first conductor circuit pattern is to be formed; and (d) forming a first conductor circuit pattern on the surface of said substrate by plating and/or sputtering a metal coating onto those regions of said substrate covered by said exposed layer of said first layer of said curable dielectric material to provide a printed circuit board of which the first layer of said dielectric material is a structural component.

In one preferred embodiment of the invention in which at least two layers of circuitry is formed, the process comprises the steps of:

(a) applying a first layer of a radiation curable dielectric material to a given area of a substrate;

(b) placing a photomask defining a first conductor circuit pattern adjacent to the surface of said first layer of said radiation curable dielectric material;

(c) exposing said material to a source of radiation and developing said material to expose those regions of said substrate where a first conductor circuit pattern is to be formed;

(d) forming a first conductor circuit pattern on the surface of said substrate by sputtering a metal coating onto those regions of said substrate covered by said exposed layer of said first layer of said curable dielectric material;

(e) applying a plating resist onto the surface of said first layer of said radiation curable dielectric material and/or onto said first conductor circuit pattern;

(f) placing a photomask defining a second conductor circuit pattern adjacent to the surface of said plating resist, and exposing and developing said resist to expose those regions of said surface of said first layer of said radiation curable dielectric material and/or said first conductor circuit where said second conductor circuit pattern is to be formed; and (g) forming said second surface conductor circuit pattern upon the surface of said first layer of said radiation curable dielectric material in electrical connection with said first conductor circuit pattern by plating a metal coating onto the exposed regions of said first layer of said radiation curable dielectric materials.

In yet another preferred embodiment of this invention, the process of this invention comprises:

(a) applying a first layer of a radiation curable dielectric material to a given area of a substrate having an electrically conductive surface;

(b) placing a photomask defining a first conductor circuit pattern adjacent to the surface of said first layer of said radiation curable dielectric material;

(c) exposing said material to a source of radiation and developing said material to expose those regions of said substrate where a first conductor circuit pattern is to be formed;

(d) sputtering a metal coating onto those regions of said substrate covered by said exposed first layer of said radiation curable material where said first conductor circuit pattern is to be formed and onto the surfaces of said unexposed first layer of said radiation curable material;

(e) applying a first layer of a plating resist to the surface of said sputtered metal layer;

(f) placing a photomask defining said first conductor circuit pattern adjacent to the surface of said first layer of said plating resist, and exposing and developing said plating resist to expose those regions of said sputtered metal coating where said first conductor circuit pattern is to be formed;

(g) forming the remainder of said first conductor circuit by plating a metal layer onto those regions of said sputtered metal layer where said first conductor circuit pattern is to be formed;

(h) removing the remaining first layer of said plating resist from the surface of said sputtered metal layer to expose the surface of said sputtered metal layer coating the unexposed surface of said first layer of said curable material;

(i) applying a second layer of a plating resist to the surfaces of said sputtered metal layer coating the unexposed surfaces of said first layer of said dielectric material;

(j) placing a photomask defining a second conductor circuit pattern adjacent to the surface of said second layer of said plating resist, and exposing and developing said plating resist to remove said exposed resist from regions of said sputtered metal layer where said second conductor circuit is to be formed;

(k) forming said second conductor circuit pattern by plating metal coating onto said exposed sputtered metal layer where said second conductor circuit pattern is to be formed;

(l) removing the remainder of the second layer of said plating resist from said sputtered metal layer to expose said metal layer, and removing said exposed metal layer from the surface of said first layer of said radiation curable dielectric material to exposing said layer; and (m) applying a second layer of dielectric radiation curable material over a given area of the said second conductor circuit layer and said exposed first radiation curable layer and repeating steps (b) to (l) to form at least one additional conductor circuit layer.

Another aspect of this invention relates to the multilayer circuit board prepared by the process of this invention.

Advantageously, in practice of the present process, less steps are required per unit operation. Surface preparation of the substrate and etching thereof are virtually eliminated. The amount of wet processing is decreased since solutions used to deposit metal, such as baths and their salts, as well as rinses used in removing such contaminants as heavy metals, surfactants, oxidizing agents and the like, are avoided. Consequently, there is less waste to dispose of. Adhesion of the sputtered material is excellent in that (1) a strong bond is formed regardless of the surface material or its texture and (2) bond formation can be effected within a relatively wide operating window (e.g. over a wide range of sputtering energies and field strengths). Films deposited by sputtering exhibit exceedingly uniform coverage and thickness since there are no current density variations or catalyst nucleation site gradients to contend with. The application of chromium, a preferred adhesion agent, is more readily accomplished via sputtering than though use of plating techniques.

BRIEF DESCRIPTION OF THE DRAWINGS

A more complete understanding of the invention may be had from a consideration of the following detailed description, taken in conjunction with the accompanying drawings in which:

FIGS. 1 to 19 are sectional side views of a preferred printed circuit in accordance with the invention illustrating successive stages of a preferred embodiment of preparing the preferred printed circuit of this invention.

DETAILED DESCRIPTION OF THE PREFERRED EMBODIMENTS OF THIS INVENTION

Figure 1:
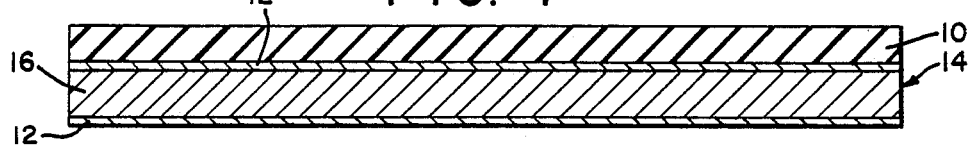

A printed circuit having high density, fine lines of printed conductors is manufactured in accordance with the process of this invention as depicted in the drawings. Referring now to FIG. 1, a layer of 10 composed of a radiation light curable dielectric material is applied to the surface 12 of a substrate 14 The nature of the useful radiation curable dielectric material can vary widely, the only requirement being that the material is radiation curable and is "non-conductive". As used herein, "non-conductive materials" are materials which are substantially non-conducting to electrical current and which are capable of functioning as a dielectric material. Usually, radiation curable dielectric materials used in the practice of this invention will have a dielectric constant of less than about 5,000, and preferably of less than about 50. In the particularly preferred embodiments of this invention, the radiation curable dielectric material of choice will have a dielectric constant of less than about 10 and in the most preferred embodiments of the invention will have a dielectric constant of less than about 5. Illustrative of useful materials which can be employed as radiation curable dielectric materials in the practice of the invention are materials which can be cured on exposure to ultraviolet radiation, infrared radiation, gamma radiation and the like forms of radiation, with those materials that are curable on exposure to ultraviolet radiation being the radiation curable material of choice. Such materials include photosensitive epoxy resins as for example those described in Japan Patents No. 8572235 and 8571628. Also useful in the practice of this invention are photosensitive siloxanes such as those described in Japan Patent No. 8534022 and photosensitive polyimides, as for example those described in Japan Patent Nos. 8542425, 85247947, 85247932, 85198537, 85135934, 8524037, 84201443, and 81120721, and European Patent No. 824171. Illustrative of still other radiation curable materials which can be used in the practice of this invention are photosensitive polyamides as for example those described in Japan Patent No. 85124624, 85180197, 85210627, 85249749, 8542425, 84212832, 84212833, 84213725, 83223149, and 83127924; photosensitive polyimide/siloxanes, as for example those described in Davis, Gary C., ACS Symp. Ser., Vol. 242, pp. 259–69 (1984), and European Patent No. 54,426; photosensitive phenolic resins and quinone diazide compounds such as those described in Japan Patent No. 81484337; photosensitive polyamide/polyimides, such as those described in Japan Patent No. 84145216; and photosensitive maleimide polymers such as those described in Japan Patent Nos. 8313630 and 82168909.

Preferred for use in the practice of this invention as radiation curable dielectric materials are ultraviolet light curable polyimides, polyamides, polyimides/polyamides, polysiloxanes, polyamide/polysiloxanes, maleimide polymers and epoxy resins, and particularly preferred for use in the practice of this invention as radiation curable dielectric materials are ultraviolet curable polyimides, polyamides and polyamides/polyimides. Amongst these particularly preferred embodiment most preferred are those embodiments in which the ultraviolet curable dielectric materials are ultraviolet curable polyimides.

While the planarity of layer 10 is not critical to the practice of this invention, layer 10 is preferably a flat substrate of substantially uniform thickness. The thickness of non-conductive layer 10 can vary widely but is not critical. However, the thickness of layer 10 is at least as thick as the desired surface conductive circuit patterns described below. In general, layer 10 is at least about 1 micron in thickness. In the preferred embodiments of this invention, the thickness of layer 10 is from about 1 micron to about 50 microns, and in the particularly preferred embodiments is from about 5 microns to about 20 microns. Amongst these particularly preferred embodiments of the invention the thickness of layer 10 is from about 15 microns to about 30 microns.

The method employed to apply layer 10 to surface 12 of substrate 14 may vary widely and any conventional method can be employed. In general, such materials will be in solution or in other liquid form which solidifies on evaporation of the solvent, or such material may be a solid. Such materials in liquid form can be applied using such conventional procedures as spinning, spraying, screen printing and the like. Solid dielectric materials may be applied to surface 12 by such conventional procedures as, for example, roller coating and the like.

Substrate 14 employed in the present invention may vary widely and can be any one of the various kinds of sheets and plates composed of metals, synthetic resins, metal clad synthetic resins, multilayer metal, glasses, and ceramics and metal coated with glass and ceramic materials, paper, cardboard, fiber, including glass cloth, wooden sheet materials or paper base phenolic resin laminate having the desired electrical and chemical properties, chemical resistance, heat resistance, and the like. Examples of useful resins are phenol formaldehyde resins, epoxy resins, melamine resins, and high melting point thermoplastic resins such as polyphenylene sulfides, polyphenylene oxides, polyimides, polyetherimides and the like. Illustrative of useful ceramics and glasses are alumina, porcelain, zirconia, silica, lithium niobate and the like. Exemplary of useful metal substrates are substrates composed of copper, nickel, cobalt, iron and alloys thereof, metal matrix composite substrates such as aluminum reinforced with graphite fibers and multilayer metal substrates such as metal coated plastics such as polyetherimides, polyphenylene sulfides and polyphenylene oxides coated with copper, nickel and aluminum, or metals such as iron, nickel, cobalt and alloys thereof coated with copper or nickel.

The metal and ceramic matrix composite material used to form substrate 14 is a class of material with controllable properties. Metal (and/or ceramic) matrix composite systems are metals (and/or ceramics) reinforced with another material in the shape of fibers, whiskers or particles. By selecting the appropriate matrix alloy and the proper type, amount and orientation of the reinforcements, it is possible to tailor the mechanical and physical properties of metal (and/or ceramic) matrix composites to a specific application. Materials having combinations of properties not seen with unreinforced metals (and/or ceramics) become possible. Such materials are discussed in detail in the publication "Metal Matrix Composites For Microwave Packaging Components", C. Thaw et al, Electronic Packaging and Production, August 1987, p. 27. These materials expand the choice of available properties over the usual polymer matrix materials (polymers reinforced with glass, aramid and quartz fibers) commonly used in printed circuit boards or other interconnects.

Metal matrix composites preferred for use as substrate 14 have a low coefficient of thermal expansion (CTE), high thermal conductivity, low density, and do not distort during machining—all of which properties are especially suited for high performance applications such as aircraft and spacecraft electronic systems. Existing metals used for electronic packaging, such as Kovar, Invar, molybdenum, aluminum and copper have at best only two of these key properties.

Major matrix materials include alloys of aluminum, magnesium, titanium and copper, while important reinforcing fibers include graphite (carbon), alumina, silicon carbide and boron carbide. Another preferred metal matrix composite system is silicon carbide particle reinforced aluminum. By varying the relative amounts of fiber and aluminum, it is possible to produce plates with CTEs ranging anywhere from near-zero to that of aluminum. This makes it possible to match the CTEs of alumina, silicon, gallium arsenide, or most any other material of interest, minimizing thermal stresses arising from CTE mismatches.

In the preferred embodiments of the invention, substrate 14 is a single or multilayer metal plate, or a metal clad synthetic resin plate in which the conductive coating is often used to form the metal ground plane of the multilayer printed circuit board whose manufacture is described in FIGS. 1 to 19. In the particularly preferred embodiments of the invention, substrate 14 is a multilayer metal plate or a metal clad synthetic resin plate in which the outer surface 12 of substrate 14 is composed of a metal normally used in the manufacture of printed circuits such as copper, nickel, chromium, palladium, platinum, silver, aluminum, gold and the like, and sandwiched core 16 is composed of a resin as described above, or of a base metal as for example, iron, nickel, molybdenum, cobalt, and the like, and alloys thereof. Outer surface 12 is preferably composed of copper, nickel, chromium or aluminum and with chromium and nickel being the particularly preferred materials. In the most preferred embodiments of the invention when ultraviolet curable polyimides are employed as the ultraviolet curable dielectric material, outer surface 12 is chromium because of enhanced adhesion between the polyimide and chromium.

Thickness of substrate 14 can vary widely and is not critical. Normally, substrate 14 can be of any thickness used for the substrates of conventional printed circuit boards. Preferably substrate 14 has a thickness ranging from about 25-2500 microns. In the more preferred embodiments of the invention, the thickness of substrate 14 ranges from about 250-1500 microns, and in the most preferred embodiments of the invention the thickness of substrate 14 ranges from about 650-850 microns.

Figure 2:
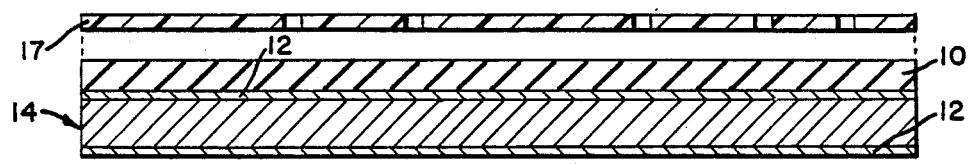

As shown in FIG. 2, in the second step of the process of this invention, photomask 17 defining a desired first interconnecting circuit pattern 26 is placed atop the ultraviolet curable material 10. Proximity or contact methods of placing photomask 17 atop material 10 may be used. In these preferred embodiments of the invention, mask 17 is placed atop the surface of layer 10 of ultraviolet curable material so that the mask 17 is in near or actual contact with the surface of layer 10.

Layer 10 is then exposed in a conventional manner to collimated light. The sources providing actinic radiation for exposure are known to those skilled in the art and are rich in ultraviolet radiation. Suitable sources are disclosed in U.S. Pat. Nos. 2,760,863, 3,649,268, 4,157,407 and 4,411,980, the disclosures of which are incorporated by reference.

Figure 3:
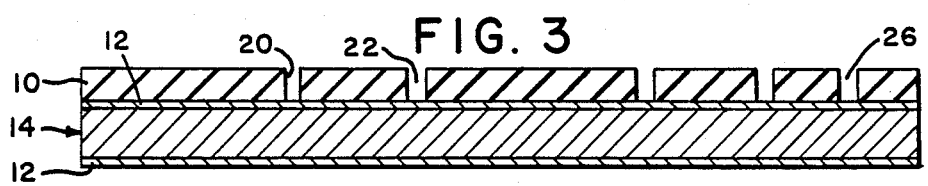

After exposure to ultraviolet radiation, the exposed layer is developed to remove portions of layer 10 from the region where interconnecting conductive circuit patterns (vias or pillars) 26 are to be formed. Because photomask 17 is brought into near or actual contact with layer 10, the collimated light exposure forms openings or vias in layer 10. As shown in FIG. 3, upon developing, walls 20 are formed at the boundaries defining cavities 22 from which the portions of layer 10 of ultraviolet curable material are removed. These walls may be straight or sloped depending on the degree of light collimation and the actinic light absorption characteristics of the exposed layer.

Figure 4:
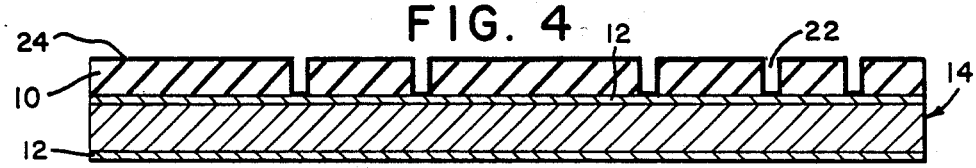

The surface of layer 10 can, optionally, be treated with a conventional wet or dry etch process to increase the adhesion of any metal deposited onto the surface by sputtering techniques. The etched surfaces of layer 10 and cavities 22 defining the interconnecting conductive circuit patterns 26 are sputtered with a conductive metal layer 24, which is composed of a conductive material such as copper, nickel, palladium, silver, aluminum, gold, platinum and the like metal used to form conductive circuits as depicted in FIG. 4. Sputtered metal layer 24 plated onto the surface 12 at the bottom of cavities 22 forms a portion of interconnecting circuit pattern 26 as will be described below. Cavities 22 may also define heat sinks or thermal columns for dissipation of heat generated through the use of the board manufactured by the process of this invention, may define shielding for electrical circuits from electromagnetic radiation or may define other elements of a printed circuit board. In the preferred embodiments of the invention, the conductive material is copper.

Useful etch processes will vary widely depending on the nature of the composition making up layer 10. Illustrative of useful etching methods are the ozone etching techniques described in U.S. Pat. Nos. 4,505,786 and 4,422,907; sulfur trioxide etching techniques described in U.S. Pat. No. 4,039,744; and nitric acid etching techniques described in U.S. Pat. No. 4,532,015 which are hereby incorporated by reference. In the preferred embodiments of the invention, when layer 10 is composed of a polyimide the surface is preferably etched with ozone or with an alcoholic alkali metal base solution, most preferably an aqueous ethanolic potassium hydroxide solution The electroless plating technique may also vary widely depending on the metal being plated. Electroless plating procedures are known to those skilled in the art, e.g., U.S. Pat. No. 4,054,483 which is incorporated by reference. Electroless plating baths are commercially available, e.g., from the Shipley Company, Revere, MA, Kollmorgen Corp., Glen Cove, NY and other sources. Useful electroless plating solutions are described in the examples of Zeblisky et al., U.S. Pat. No. 3,095,309, particularly Example II, which is incorporated by reference.

Sputtering processes for film deposition have been available for the last two decades. Usually, the target (a plate of the material to be deposited or the material from which a film is to be synthesized) is connected to a negative voltage supply. The substrate holder faces the target. The holder may be grounded, floating, biased, heated, cooled, or some combination of these. A gas, usually argon, is introduced to provide a medium in which a glow discharge can be initiated and maintained. When the glow discharge is started, positive ions strike the target plate and remove mainly neutral target atoms by momentum transfer, and these condense into thin films.

In some cases, gases or gas mixtures other than Ar are used. Usually this involves some sort of reactive sputtering process in which a compound is synthesized by sputtering a metal target (e.g. Ti) in a reactive gas (e.g., $O_2$ or $Ar$-$O_2$ mixtures) to form a compound of the metal and the reactive gas species (e.g. $TiO_2$). Reactive sputtering should not be confused with chemical sputtering in which the reactive gas (e.g., $O_2$) reacts with the target surface (e.g., C) to form volatile compounds (e.g., CO) that are pumped away.

Procedures for sputtering thin films are described in detail in "Thin Film Processes", edited by John L. Vossen and Werner Kern, Academic Press, 1987 and "Handbook of Thin Film Technology", edited by Leon I. Maissel and Reinhard Glang, McGraw Hill, 1970.

Figure 5:
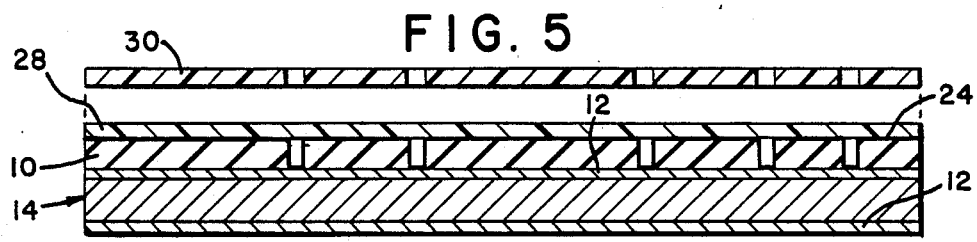
Figure 6:
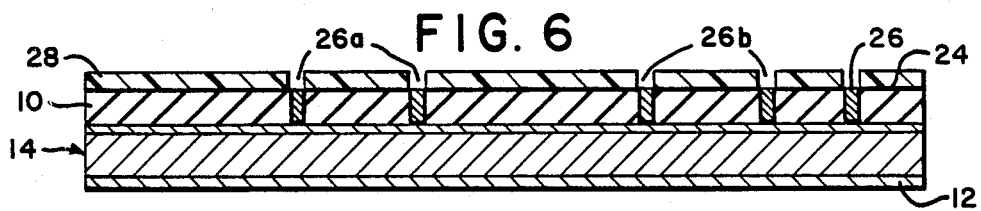

Referring now to FIGS. 5 and 6, the remainder of interconnecting circuit patterns 26 is formed atop layer 24 in the bottom of cavities 22 by plating techniques. As noted above, portions of pattern 26 may form a portion of element 26(a) which is depicted in the figures as heat thermal columns for dissipation of heat generated during the operation of the board. The further fabrication of thermal columns 26(a) will be depicted below. Other portions of pattern 26 may form shielding elements 26(b) for shielding circuits from electrical interference. In this step of the process of this invention, as depicted in FIG. 5, layer 28 composed of a photoresist or other photosensitive material of suitable uniform thickness (preferably a solid photoresist) is applied to metal layer 24 using conventional techniques covering open areas or voids 22. Useful photoresist or other photosensitive materials can vary widely, and include dry photoresist as for example such dry photoresist available commercially from Dupont under the trademark Riston, from MacDermid under the trademark UltraMac, and from Dynachem, a subsidiary of the Thiokol Company, under the trademark Laminar, and the like. Also useful in the practice of this invention are wet photoresist as for 1 example such wet photoresist available from W.R. Grace Co. under the trademark Accutrace 1000 and available from Dexter Hysol under the trademark PR 7550 Blue and PR 7500 Blue. Preferred for use in the practice of this invention are dry photoresists.

The thickness of photoresist layer 28 is not critical and may vary widely. Photoresist layer 28 may be of any thickness known to those of skill in the art. Preferably, the thickness of photoresist layer 28 is at least as thick as the desired circuit pattern and is at least about 0.001 mm in thickness. In the preferred embodiments of the invention, the thickness of photoresist layer 28 is about 0.0051-0.257 mm, and in the particularly preferred embodiments of the invention is from about 0.013 mm to about 0.1 mm.

As shown in FIG. 5, photomask 30 defining a desired interconnecting conductive circuit pattern 26 is placed in intimate contact with photoresist layer 28 in intimate contact therewith such that the pattern of photomask 30 is in congruence with voids 22. Mask 30 is again placed in near or actual contact with photoresist layer 28. Masked photoresist layer 28 is then exposed to a source of actinic radiation (not depicted) and developed to open areas or voids 22 where the interconnecting conductive circuit 26, thermal columns 26(a) and shielding element 26(b) are to be formed (See FIG. 6). The remainders of interconnecting conductive circuit 26, thermal columns 26(a) and shielding element 26(b) are then formed by plating a metal layer into voids 22 on top of sputtered layer 24 using conventional techniques, as for example, those techniques described in "Thin Film Processes", John L. Vossen and Werner Kern, Academic Press, 1978. Because the formation of interconnecting conductive circuit pattern 26, thermal columns 26(a) and shielding elements 26(b) even through they are referred to as a plated metal layer, or as a metal layer formed by plating, they when formed of the same metal, as for example, copper, in fact form a metallurgically integral, continuous structure whenever overlapping of plating layers in immediately continuous layers occur, and a high quality electrically and thermally conductive path exist between all interconnected conductive patterns.

Figure 7:
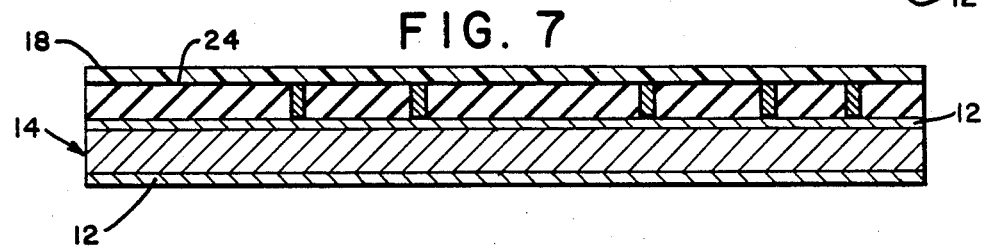
Figure 8:
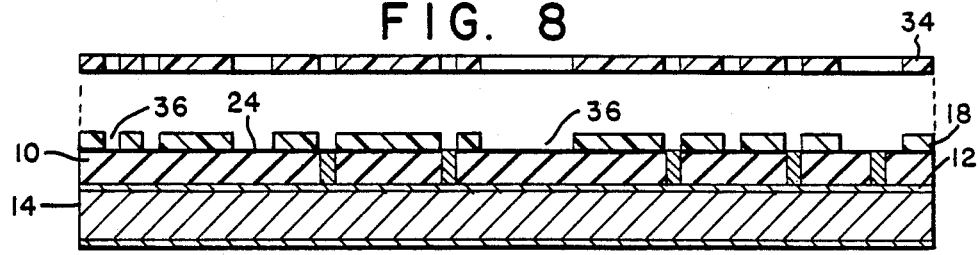
Figure 9:
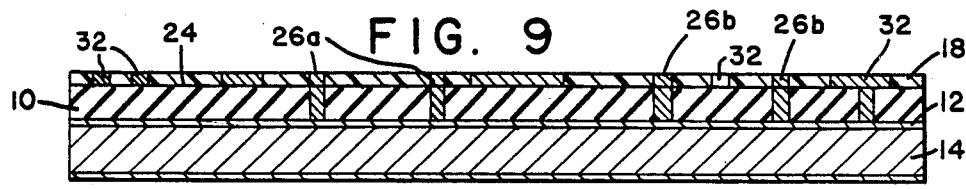
Figure 10:
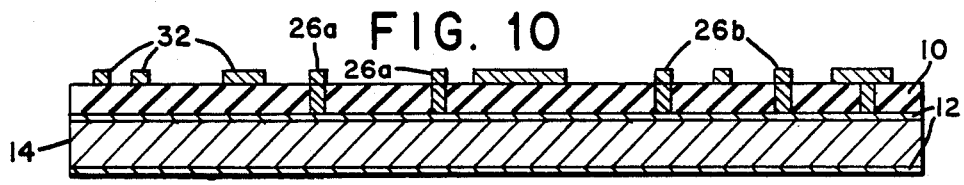

Referring to FIG. 7, upon formation of interconnecting conductive circuit 26, remaining photoresist layer 28 is completely stripped from the partially manufactured printed circuit (not shown), and a new photoresist layer 18 is applied to the surface of the sputtered metal layer 24 and to the surface of interconnecting circuit pattern 26. As shown in FIGS. 8, 9 and 10, a first surface conductor pattern 32, can be formed on the surface of ultraviolet curable layer 10. First surface conductor circuit pattern 32 may have any desired shape and as illustrated in the figures is in fact interconnected by interconnecting conductive circuit pattern 26 to electrically conductive circuit 12 of substrate 14. In this mode, surface 12 may function as a ground plane. First surface conductive pattern 32 is formed using substantially the same process as that used to form first interconnecting conductive circuit pattern 26 by depositing a photoresist layer 18 of suitable thickness onto the surface of sputtered metal layer 24, placing a photomask 34 having the desired surface conductive circuit pattern atop photoresist layer 18, exposing photoresist layer 18 through mask 34 and developing photoresist layer 18 to define areas or voids 36 where first surface conductive circuit pattern 32 is to be formed. As shown in FIG. 8, thin sputtered metal layer 24 is deposited upon the surface of layer 10 in contact with interconnecting conductive circuit pattern 26 to form a good conductive base throughout the area on which first surface conductive circuit pattern 32 is formed. Layer 24 allows formation of circuit 32 by faster plating techniques.

As shown in FIG. 9, a metal coating is plated within voids 36 to a thickness of photoresist layer 18 to form first surface conductive circuit 32, and a portion of thermal columns 26(a) and a portion of shielding elements 26(b). Because plating is used for formation of the conductive circuit patterns, even though they are referred to as separate layers, they in face form a metallurgically integral, continuous copper structure wherever overlapping of conductive circuit patterns in immediately contiguous circuit layers occurs and a high quality electrically and/or thermally conductive path thus exists between all interconnected conductive patterns.

Remaining photoresist layer 18 is stripped from the surface of sputtered metal layer 24. After removal of remaining photoresist layer 18 (not shown) and before formation of second ultraviolet curable dielectric layer 38 (see FIG. 11), the unwanted regions of thin sputtered metal layer 24 are removed by a rapid conventional metal etch to prevent short circuits to form the structure of FIG. 10. The sputtered metal layer 24 is sufficiently thin and surface conductive circuit layer 32 is sufficiently thick so that there is no appreciable effect on the thickness of patterns 26 and 32, thermal columns 26(a) and shielding elements 26(b).

Figure 11:
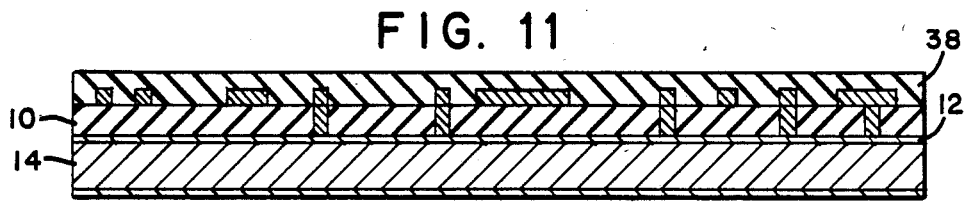
Figure 12:
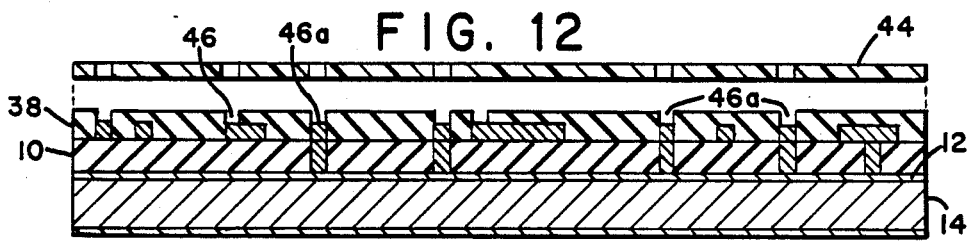

A second interconnecting conductor circuit pattern 42 (shown in FIG. 15) is formed using substantially the same techniques described below in FIGS. 1 to 7 to form first interconnecting conductive circuit pattern 26. As in the procedure of FIGS. 1 to 3, a second layer 38 of an ultraviolet curable dielectric material is applied to the surface of circuits 32, column 26(a), element 26(b) and layer 10 as shown in FIG. 11. Photomask 44 having a suitable circuit pattern is placed atop layer 38, layer 38 is exposed through mask 44 and layer 38 is developed to define open areas or voids 46 where second interconnecting circuit pattern 42 will be formed and voids 46(a) for continuation of thermal columns 26(a) and shielding element 26(b), as depicted in FIGS. 11 and 12.

Figure 13:
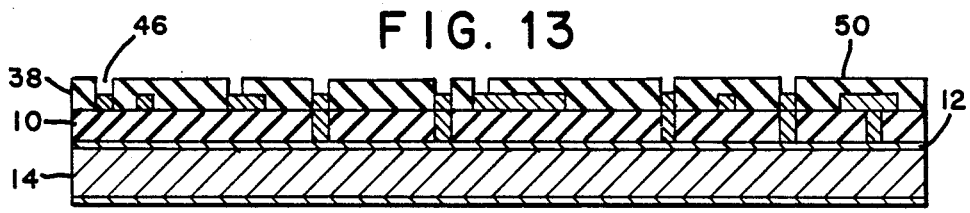

A thin sputtered metal layer 50 preferably chromium is deposited onto layer 38 and the surface of voids 46 to form a continuous conductive plane throughout the area on which second interconnecting conductive circuit pattern 42 will be formed as depicted in FIG. 13. As shown in FIGS. 13, 14, 15, photoresist layer 54 is deposited atop layer 50 covering voids 46 and 46(a), a photomask 54(a) defining the same circuit pattern as photomask 44 is placed atop layer 54. Photoresist layer 54 is then exposed to ultraviolet radiation and developed to open voids 46 and 46(a). Second interconnecting conductive circuit pattern 42 and portions of thermal columns 26(a) and shielding element 26(b) can then be plated within voids 46 and 46(a) to a thickness substantially equal to the thickness of second ultraviolet curable layer 38 as depicted in FIG. 15.

Second surface conductive circuit pattern 52 is formed using substantially the same techniques employed depicted in FIGS. 7 to 10 to form first surface conductive circuit pattern 32. In this procedure, remaining photoresist layer 54 is removed from metal layer 50 (not shown). A layer of dry film photoresist is deposited atop sputtered metal layer 50, a photomask 56 is placed atop photoresist layer 54(b), photoresist layer 54(b) is exposed through mask 56, and photoresist layer 54(b) is developed to define open areas or voids 58 where the second surface conductive circuit pattern 52, and voids 60 for continuation of thermal columns 26(a) and shielding elements 26(b) is to be formed as depicted in FIG. 16. A metal layer can then be plated within voids 58 and 60 to a thickness equal to the thickness of photoresist layer 54(b) to form pattern 52, column 26 (a) and element 26(b) as depicted in FIG. 17. The remaining photoresist layer 54(b) is removed, and then a rapid etching operation removes unwanted portions of thin sputtered metal layer 50 to provide structure depicted in FIG. 18. Sputtered metal layer 50 is sufficiently thin and second surface conductive circuit 52 and thermal columns 26(a) and shielding elements 26(b) are sufficiently thick so that the etching operation has no appreciable effect on the thickness of the latter. The printed circuit board depicted in the figures is then completed by application of third layer 60 of a permanent dielectric substrate to the top circuit layer which is second surface conductive circuit 52 in the present example. Interconnect circuits 62 for electrically connecting the surface mounted device 64 to the internal circuitry of the board, and to thermal columns 26(a) can be formed through layer 60 using the techniques used in the formation of first and second interconnect circuit layers 52 and 26, respectively, described above, to complete the manufacture of the printed circuit illustrated in FIG. 19.

The present example in which multilayer boards having four and five layers of conductive circuits been provided for illustrative purposes only. It should be appreciated that, if desired, additional circuit layers and other elements such as additional thermal columns and shielding elements, can be formed using the above-described methods prior to application of dielectric layer 60 to the top circuit layer. It will be apparent to a person skilled in the art that other embodiments and various modifications to the details of fabrication shown and described above may be made without departing from the scope of this invention.

What is claimed is:

1. A process for manufacturing a printed circuit board which comprises the steps of:
   (a) applying a first layer of a radiation curable dielectric material to a given area of a substrate;
   (b) placing a photomask defining a first conductor circuit pattern adjacent to the surface of said first layer of said curable dielectric material;
   (c) exposing said material to a source of radiation and developing said material to expose those regions of said substrate where a first conductor circuit pattern is to be formed;
   (d) forming a first conductor circuit pattern on the surface of said substrate by sputtering a metal coating over those regions of said substrate covered by said exposed first layer of said curable material to provide a printed circuit board of which the first layer of said dielectric material is a structural element, aid forming step (d) comprising steps (e) to (i);
   (e) sputtering a metal coating onto the exposed surfaces of said substrate where said first conductor circuit pattern is to be formed thereby forming a portion of said first circuit pattern, and sputtering said coating onto the surface of said first layer of said dielectric material;
   (f) applying a first layer of a plating resist to said coating;
   (g) placing a photomask defining said first conductor circuit pattern adjacent to the surface of said first layer of said resist;

(h) exposing said resist to a source of radiation and developing said resist to expose those regions of said substrate where a first conductor circuit pattern is to be formed;

(i) plating a second metal coating onto those regions of said sputtered metal coating where said circuit pattern is to be formed forming the remainder of said first conductor circuit pattern;

(j) forming a second conductor circuit pattern on the surface of said first layer of said radiation curable material, said second conductor circuit pattern forming step (j) comprising steps (k) to (o);

(k) removing the remainder of said first plating resist and applying a second layer of plating resist to the surface of said sputtered coating and to said first conductor circuit pattern;

(l) placing a photomask defining a second conductor circuit pattern adjacent to the surface of said second layer of said resist;

(m) exposing said second layer of said plating resist to a source of radiation and developing said resist to expose those regions of said sputtered coating and/or said first conductor circuit pattern where said second conductor circuit pattern is to be formed;

(n) forming said second conductor circuit pattern by plating a metal coating onto the exposed regions of sputtered metal coating and/or said first conductor circuit pattern; and (o) removing plating resist from the surface of the sputtered metal layer which does not form a part of said second conductor circuit pattern, and removing said metal layer to expose the surface of said first layer of radiation curable dielectric material.

2. A process according to claim 1 which further comprises repeating steps (a) to (d) to form a circuit board having at least one additional circuit pattern and at least one additional layer of a radiation curable dielectric material.

3. A process according to claim 1 wherein said metal coating is sputtered onto said exposed regions by ion beam or magnetron sputtering.

4. A process according to claim 1 wherein said second conductor circuit pattern is formed by electroplating said metal coating onto said exposed regions.

5. A process according to claim 1 which further comprises step (p) applying a second layer of radiation curable dielectric material to a given area of said exposed surfaces of said first layer of radiation curable dielectric material and to a given area of said second conductor circuit pattern and/or said second conductor circuit pattern.

6. A process according to claim 5 wherein the exposed surfaces of said first layer of said material is etched prior to application of said second layer of said material.

7. A process according to claim 1 which further comprises repeating steps (a) to (i) to form at least one additional conductor circuit pattern.

8. A process according to claim 1 which further comprises repeating steps (a) to (o) to form at least two additional conductor circuit patterns.

9. A method according to claim 1 wherein said material is selected from the group consisting of polyimides, polyimides/polyamides, polysiloxanes, polyamide/polysiloxanes and epoxy resins.

10. A method according to claim 9 wherein said materials are selected from the group consisting of polyimides and polyimides/polyamides.

11. A method according to claim 10 wherein said materials are selected from the group consisting of polyimides.

12. A method according to claim 1 wherein dielectric constant of said material is less than about 5,000.

13. A method according to claim 12 wherein said dielectric constant, is less than about 50.

14. A method according to claim 13 wherein said dielectric constant is less than about 10.

15. A method according to claim 14 wherein said dielectric constant is less than about 5.

16. A method according to claim 1 wherein said substrate is a metal plate.

17. A method according to claim 16 wherein said substrate comprises a multi layer metal plate.

18. A method according to claim 17 wherein the outer metal layer is composed of nickel or copper.

19. A method according to claim 17 wherein said outer metal layer is composed of nickel.

20. A method according to claim 19 wherein said layer is composed of copper.

21. A process for manufacturing a multilayer printed circuit board which comprises the steps of:

(a) applying a first layer of radiation curable dielectric material to a given area of a substrate:

(b) placing a photomask defining a first conductor circuit pattern adjacent to the surface of said first layer of said curable dielectric material;

(c) exposing said material to a source of ultraviolet radiation and developing the exposed material to remove said exposed materials from regions of said substrate forming voids in said material where a first conductor circuit pattern is to be formed;

(d) sputtering a metal coating onto those regions of said substrate defining said voids thereby forming a portion of said first conductor circuit pattern, and sputtering said metal coating onto the surfaces of said unexposed first layer of said ultraviolet curable material;

(e) applying a first layer of a plating resist to the surface of said first layer of said ultraviolet curable dielectric material:

(f) placing a photomask defining said first conductor circuit pattern adjacent the surface of said first layer of said plating resist, the pattern defined by said photomask being congruent with the voids in said first layer of said ultraviolet curable material;

(g) exposing and developing said resist to remove said exposed resist from regions of said surface of said sputtered metal coating defining said voids:

(h) forming the remainder of said first conductor circuit pattern by plating a second metal coating upon the surface of said sputtered metal layer defining said voids;

(i) removing the remainder of said first layer of said plating resist from the surface of said sputtered metal coating to expose the surface of said sputtered metal coating covering the unexposed surface of said first layer of said curable material:

(j) applying a second layer of a plating resist to the surfaces of said exposed sputtered metal coating:

(k) placing a photomask defining a second conductor circuit pattern adjacent to the surface of said second layer of said plating resist, and exposing and developing said resist to remove said exposed resist from regions of said sputtered metal coating where said second conductor circuit is to be formed:

(l) forming said second conductor circuit pattern by plating a second metal coating onto said exposed sputtered metal coating where said second conductor circuit pattern is to be formed:

(m) removing the remainder of said second layer of said plating resist from the surface of said sputtering metal coating to expose said metal layer, and removing said exposed metal coating from the surface of said first dielectric radiation curable layer to exposing said layer: and (n) applying a second layer of dielectric radiation curable material over a given area of the said first conductor circuit pattern, said second conductor circuit pattern and/or said exposed first radiation curable layer and repeating steps (b) to (l) to form at least one additional conductor circuit layer.

* * * * *

UNITED STATES PATENT AND TRADEMARK OFFICE
CERTIFICATE OF CORRECTION

PATENT NO. : 4,921,777                  Page 1 of 2

DATED : May 1, 1990

INVENTOR(S) : H.A. Fraenkel et al.

It is certified that error appears in the above-identified patent and that said Letters Patent is hereby corrected as shown below:

Col. 1, line 39-40: "printing" should read -- plating --.

line 44: After "patterns", add a period.

Col. 9, line 3: After "solution", add a period.

line 66: "for 1 example" should read -- for example --.

Col. 10, line 30: "Because the formation" should read -- Because plating is used in the formation --.

Col. 12, line 56: "aid" should read -- said --.

Col. 14, line 4: "wherein dielectric" should read -- wherein the dielectric --.

line 7: After "constant", delete the comma.

line 18: "17" should read -- 18 --.

UNITED STATES PATENT AND TRADEMARK OFFICE
CERTIFICATE OF CORRECTION

PATENT NO. : 4,921,777

DATED : May 1, 1990

INVENTOR(S) : H.A. Fraenkel, et al

It is certified that error appears in the above-identified patent and that said Letters Patent is hereby corrected as shown below:

Col. 14, line 24:   "radiation" should read -- an ultraviolet--.

line 25:   After "substrate", add -- having an electrically conductive surface--.

Signed and Sealed this

Fifth Day of November, 1991

*Attest:*

HARRY F. MANBECK, JR.

*Attesting Officer*      *Commissioner of Patents and Trademarks*